United States Patent [19]

Clark

[11] Patent Number: 5,397,361
[45] Date of Patent: Mar. 14, 1995

[54] CRANIOPLASTY SURGICAL PROCEDURE AND KIT

[75] Inventor: Dennis E. Clark, Waterloo, Iowa

[73] Assignee: Surgical Prosthetics Resource, Inc., Waterloo, Iowa

[21] Appl. No.: 82,267

[22] Filed: Jun. 23, 1993

[51] Int. Cl.$^6$ ............................................... A61F 2/28
[52] U.S. Cl. ................................... 623/16; 623/901; 433/214; 264/222; 264/DIG. 30
[58] Field of Search ................. 433/214; 623/16, 901; 264/222, 223, 227, DIG. 30

[56] References Cited

U.S. PATENT DOCUMENTS

| | | | |
|---|---|---|---|
| 1,027,016 | 5/1912 | Volnagel . | |
| 1,556,802 | 10/1925 | Page | 264/223 |
| 1,700,844 | 2/1929 | Hess | 264/157 |
| 2,907,067 | 10/1959 | Burger | 264/223 |
| 4,335,067 | 6/1982 | Castanis et al. | 264/222 |
| 4,708,836 | 11/1987 | Gain et al. | 264/40.1 |
| 4,828,116 | 5/1989 | Garcia | 206/575 |
| 4,941,212 | 7/1990 | Liff | 2/206 |
| 5,076,438 | 12/1991 | Aronson | 206/557 |
| 5,108,686 | 4/1992 | Griffin | 264/222 |
| 5,124,106 | 6/1992 | Morr et al. | 264/221 |
| 5,218,975 | 6/1993 | Prostkoff | 623/16 |

*Primary Examiner*—Paul Prebilic
*Attorney, Agent, or Firm*—Zarley, McKee, Thomte, Voorhees & Sease

[57] ABSTRACT

A process of producing a cranial plate duplicating the dimensions of an excised portion of the cranium comprising, obtaining an excised portion of the cranium of a patient, preparing a three-dimensional impression of the excised portion in an impression material, removing the excised portion of the patient's cranium from the impression material to provide a mold cavity, and thereafter filling the cavity with a sterile resinous material which sets, and thereafter removing the set resinous material to form a plate duplicating the dimensions of the excised portion of the patient's cranium, and finally surgically installing the plate in the patient's cranium to replace the excised portion of the cranium earlier removed.

12 Claims, No Drawings

CRANIOPLASTY SURGICAL PROCEDURE AND KIT

FIELD OF THE INVENTION

This invention relates to the field of cranioplasty surgery. It relates further to a kit and process for exactly reproducing an excised portion of a patient's skull. As a result an artificial skull piece of exact dimensions to that earlier surgically removed may be made for replacement use.

BACKGROUND OF THE INVENTION

Surgical efforts to repair cranial defects commonly occur. For example, various types of surgical procedures on the human brain require removal of a portion of the skull. By way of example only, those include surgeries that remove brain tumors, surgeries to reduce brain swelling, and surgeries required to reconstruct damaged portions of the skull.

In many of these surgeries it is of course most desirable that when the successful surgery is completed that the patients own skull plate be returned intact. There are many occasions however where this is simply not possible. Perhaps the most common example is those instances where there are good medical reasons why the removed skull plate needs to be stored for long periods of time. A typical example would be with brain swelling that is relieved by removal of a portion of the skull. This may necessitate a long time between removal and replacement. In typical procedures where skull portions are removed, they must be replaced within an eight week period or the infection risk becomes too high. Therefore the removed skull plate simply cannot be returned.

In those cases that the skull plate cannot be returned, either because it has been removed for such a prolonged period or because it has been damaged, it is necessary to insert an artificial skull plate. Such artificial skull plates are normally prepared on the spot in surgery using a plastic resinous material that is moldable for a brief period and then sets. A typical example of such a material is one sold under the trademark, CRANIOPLASTIC, by the L. D. Caulk Co., Division of Dentsply International Inc., of Milford, Del. 19963.

These resinous materials for repairing cranial defects generally consist of a powder component and a liquid component. They are maintained in sterile condition and mixed during the course of the surgery. After mixing the two monomers there is a doughing time during which kneading occurs, perhaps four to five minutes, at which time the material becomes dough like and capable of handling for a period that varies depending upon temperature, but usually for about six to eight minutes. During a typical operation the surgeon hand molds the material during this period of time followed by a setting time of thirteen to fifteen minutes. In this brief period of time the physician, by hand, molds the prosthesis to conform to the cavity in the skull as best he can, it sets, and then he may have to further alter it by grinding, and the prosthesis is then sutured into the skull.

Obviously under the pressure of surgery and by use of the hand technique, it is impossible for the surgeon to obtain precise conformity with the skull cavity left by removal of the patient's own cranial plate. Thus, at best, even the most skilled surgeons can provide only an approximation of conformity. Moreover, with time pressure between the doughing period and the setting period. The surgeon must work as fast as possible under the constant pressure of the knowledge that if he does not complete his work within six to eight minutes the material will set and become unworkable. When this occurs another attempt must be made to provide a satisfactory prosthesis.

As a result of the above situation confronting surgeons during cranioplasty surgery, two common results occur. In the first instance in almost all cases the prosthetic skull plate is at best an approximation to the patient's excised skull plate. In the second instance, time in the operating room is lengthened considerably because of the time involved in the hand formation of the skull plate, the time involved in setting of the plate, and if there are failures, the time involved in repeating the process. At typical surgical room hourly billing rates one can see that the expense is considerable. Moreover, since there are approximately 60 to 80 thousand of these procedures that occur annually, it can be seen that the increased expense is enormous. Moreover the resulting prosthesis is often a very poor duplication of the removed patient's cranial plate. This of course means that the fit is imperfect, which may cause its own subsequent patient problems.

Accordingly, it is an object of this present invention to provide an improvement in the cranioplasty surgical procedure, wherein operating time is reduced and as well an excised portion of a patient's skull can be replaced with a virtual duplicate of the patient's removed cranial plate.

Another object of the present invention is to provide a process for making a reproduction of excised portion of a patient's skull, utilizing an impression material in conjunction with a resinous CRANIOPLASTIC material.

Another object of the present invention is to provide a kit usable in conjunction with cranioplasty surgery, which contains a sterile resinous material portion for repairing cranial defects and separately packaged an impression material usable for making a 3-dimensional mold cavity of an excised portion of a patient's skull, and finally, instructions for use of the two materials to provide duplication of the patient's removed skull portion.

The method and manner of accomplishing each of the above objectives will become apparent from the detailed description of the invention which follows hereafter.

SUMMARY OF THE INVENTION

A process and kit for use in cranioplasty. It allows duplication of a skull plate prior to the replacement surgery. As a result an exact duplicate is made and the surgery time and risk reduced.

DETAILED DESCRIPTION OF THE INVENTION

The kit includes a container which may be of any suitable dimension, and made from any suitable material such as cardboard or the like. In the container, various items are provided for carrying out the process.

In particular a typical container might contain instructions for use of all the materials, coded to each of the materials, a separately packaged sterile impression material used for making an impression of an excised portion of a patient's skull, a separately packaged a small amount of sterile water usable with the impression material, three small mixing bowls perhaps in nested relationship each approximately cup size in diameter, two small mixing spatulas, and as well those items normally included in a CRANIOPLASTIC kit of material obtained from L. D. Caulk Co., in particular a liquid monomer package and a separate powder resin component package. The entire contents of the kit should be sterile.

The process will now be described assuming that initially in some surgical procedure it has been necessary for a surgeon to excise a portion of the patient's skull as a part of a normal surgical procedure. It is also assumed that for whatever reason, the excised skull portion can not be returned when the surgical procedure is completed, thus necessitating use of an artificial skull plate.

As earlier indicated, the normal useful life a removed skull plate is approximately eight weeks. During the time that the removed skull plate is away from the patient, the above-described kit provides the means by which an exact duplicate may be prepared, under conditions of substantially less pressure.

In particular, the impression material is initially used with the skull plate in order to make a 3-dimensional mold of the skull plate. The preferred impression material is a product known commercially in the field as "alginate". It is commonly available. The most common use for alginate now is use by dentists for creating tooth impressions. A variety of sources for alginate are commercially available. A common one is COE Laboratories, Inc. of 3737 West 127th Street, Chicago, Ill. 60858. In short, any of the impression materials commonly used for dental impressions is suitable. Alginate comprises a salt of alginic acid and on a weight basis from 7% to 13% calcium sulfate, from 30% to 60% crystalline silica, from 1% to 5% zinc oxide, from 1% to 5% potassium titanium fluoride, and from 1% to 5% of tetra sodium pyrophosphate.

This impression material is mixed by mixing the powder and water at approximately room temperature, 72° F. (approximately 22° C.). The product will normally gel in about three minutes. Generally cold water retards gelation and warm water hastens gelation. The ratio of water to powdered impression material or alginate should be from 4.59 ml to 16.15 g up to 6.21 ml to 21.85 g, preferably from 5.4 ml to 19.0 g. The material is mixed vigorously with a stiff spatula until the consistency is smooth. This normally would require about thirty to forty seconds. The material is then loaded into a tray before gelation begins. The tray is filled approximately half full with the mixed alginate material. Immediately the patient's skull plate or natural cranial section is laid in the tray, concave side up. The alginate material is allowed to set up for approximately three minutes, during which time additional alginate material is mixed in similar fashion to that earlier described. The freshly mixed alginate material is then poured on top of the first alginate material and over the cranial segment and allowed to stand for a setting period of approximately three to five minutes. Because of the difference in times of mixing of each portion, the onset of setting for the two poured portions of alginate differ. Thus the two layers formed can be separated to provide a lower mold half and an upper mold half. The cranial segment is removed leaving behind a set impression material which when the two halves are placed together provides a cavity of exact duplication of the patient's removed skull plate.

This alginate mold comprising a top mold half and a bottom mold half of the cranial piece is useful for several attempts at duplication of the natural skull piece with a CRANIOPLASTIC material. However, after a few uses, it should not be used further, as it does have a tendency to shrink-after time.

With the mold in hand, the CRANIOPLASTIC duplication is now ready to proceed. In particular, a CRANIOPLASTIC resinous material commonly used such as that supplied by L. D. Caulk Co., as earlier described, can be used. As known to those skilled in the art there are basically two types of resin, the first a slow setting poly methyl methacrylate resin and the second a faster setting resin. Either can be used, at the artisan's choice.

These comprise a powdered component composed of: methyl methacrylate polymer 79.6 weight, methyl methacrylate-styrene copolymer 19.9% weight, benzoyl peroxide 0.5% weight; and, a liquid component composed of: methyl methacrylate monomer 95.05% volume, ethylene dimethacrylate monomer 4.28% volume, dimethyl p-toluidine 0.66% volume, hydroquinone 20±5 ppm is also provided in the kit for disinfection.

A dose of CRANIOPLASTIC resin is prepared by mixing the entire contents of one pouch (30 g) of powder (methyl methacrylate polymer, methyl methacrylate-styrene copolymer and benzoyl peroxide) and one ampul (17 ml) of the liquid monomers (methyl methacrylate, ethylene dimethacrylate). Depending upon the extent of the surgical procedure and the technique employed, one to two doses may be required. Each required dose should be mixed separately.

Mixing should be done only in a well ventilated area. Two pairs of gloves should be used while mixing. Heat accelerates the doughing time and the setting time; therefore, the product should be at room temperature (23° C.-73° F.) before mixing. Under sterile conditions and techniques, the entire contents of the powder pouch are emptied into a small sterile stainless steel mixing bowl or a sterile glass jar (60 ml). Then the entire contents of the liquid ampul are added. Next one should stir with a spatula until the powder is completely wetted with the liquid (approximately 30 seconds).

In accordance with the above, after the material has been mixed and before it becomes dough-like, but is still thoroughly mixed, the material is poured into the recessed area of the bottom one-half of the impression mold, with the two halves then being joined. They are maintained together for approximately 20 minutes to allow the CRANIOPLASTIC material to cure. The curing time is typically 20-30 minutes at room temperature. It is, of course, dependent upon both temperature of the resin and the size of the prosthesis. At this point the molds are removed and a cranial prosthesis, of virtual exact duplication of the patient's own skull piece results. This provides duplication of even the interior side indentations caused by tissue. Any sharp edges that might remain on the prosthesis from the mold are smooth and the device is now ready for surgery.

The skull prosthesis is then sent to the physician for use. Surgery is then scheduled at the convenience of both the surgeon and the patient. During the surgery process no time is taken for molding, the pressure of on-the-spot performance by the surgeon to mold a piece as best as possible is eliminated, and the skull piece can merely be fit, sutured, bonded to the skull as needed, and the surgery ended. Thus, the skull piece is of exact conformance and the amount of surgery time is minimized.

It can therefore be seen that the invention accomplished all of its stated objectives.

It is intended that the kit is disposable and that it will be purchased containing the combination of the alginate material for the impression mold and the CRANIOPLASTIC material for creating the skull piece. To this end, the materials earlier described, together with trays, may all be packaged in the kit. Instructions on use of each, of course will go along with the material.

Although the process and the kit have been described in a practical and preferred embodiment, it will be appreciated that departures may be made within the spirit and scope of this invention which should, therefore, not be limited except as set forth in the claims which follow giving due consideration to the literal language of the claims and the doctrine of equivalence.

What is claimed is:

1. A process of producing a cranial plate duplicating the dimensions of an excised portion of the cranium, said process comprising;

obtaining an excised portion of the cranium of a patient;

preparing a 3-dimensional impression of said excised portion of the cranium in an impression material;

removing the excised portion of the patient's cranium from the impression material to provide a mold cavity of the excised cranial portion of the patient;

filling said mold cavity of said impression material with a sterile resinous material;

allowing the resinous material to set;

removing the set resinous material which is in the form of a plate duplicating the dimensions of the excised portion of the patient's cranium; and, surgically installing said plate to the cranium of the patient from whom the excised portion of the cranium was removed.

2. The process of claim 1 wherein the impression material is an alginate impression material.

3. The process of claim 1 wherein the mold cavity has a top half and a separable bottom mold half.

4. The process of claim 2 wherein the alginate impression material while still pourable and before it becomes dough-like is poured in the bottom mold half with the two halves being joined to prepare an impression of the excised portion of the cranial plate.

5. The process of claim 4 wherein the mold after being joined is allowed to set for at least three minutes.

6. The process of claim 5 wherein the sterile resinous material is a polymethylmethacrylate resin.

7. The process of claim 6 wherein the sterile resinous material is allowed to cure in the impression mold for from 20 to 30 minutes.

8. A method of performing cranioplasty surgery, comprising:

removing a cranial plate from a patient;

preparing prior to any replacement surgery for said plate an exact duplicate of the removed patient's own cranial plate; and thereafter, surgically replacing the removed plate with a precast prosthesis duplicate of the removed plate.

9. The method of claim 8 wherein the impression material is an alginate impression material.

10. The method of claim 9 wherein the mold cavity has a top half and a separable bottom mold half.

11. The method of claim 10 wherein the alginate gel material while still pourable and before it becomes dough-like is poured partially in the top mold half and partially in the bottom mold half with the two halves being joined to prepare an impression of the excised portion of the cranial plate.

12. The method of claim 11 wherein the mold after being joined is allowed to set for at least three minutes.

* * * * *